United States Patent [19]
Brownlee et al.

[11] Patent Number: 5,360,422
[45] Date of Patent: Nov. 1, 1994

[54] WASHABLE DIAPER WITH LIQUID IMPERVIOUS CHANNEL FOR RETAINING DISPOSABLE ABSORBENT INSERT

[75] Inventors: James R. Brownlee, West Vancouver; William E. Lasby, White Rock, both of Canada

[73] Assignee: Caring Products International, Inc., Vancouver, Canada

[21] Appl. No.: 970,880

[22] Filed: Nov. 3, 1992

Related U.S. Application Data

[63] Continuation-in-part of Ser. No. 944,279, Sep. 14, 1992, which is a continuation-in-part of Ser. No. 921,579, Jul. 30, 1992, abandoned.

[51] Int. Cl.⁵ ............................................. A61F 13/15
[52] U.S. Cl. ............................... 604/385.2; 604/387; 604/393; 604/397
[58] Field of Search .................. 604/385.2, 386–387, 604/393–398, 400

[56] References Cited

U.S. PATENT DOCUMENTS

| | | | |
|---|---|---|---|
| 2,026,158 | 12/1935 | Bennett | 128/290 |
| 2,319,138 | 5/1943 | Kneibler | 2/234 |
| 2,369,773 | 2/1945 | Brenner | 2/224 |
| 2,381,232 | 8/1945 | Stone | 2/43 |
| 2,476,585 | 7/1949 | Cohen | 2/43 |
| 2,522,009 | 9/1950 | Wohlman | 128/288 |
| 2,532,029 | 11/1950 | Medoff | 604/394 |
| 2,556,800 | 6/1951 | Donovan | 604/394 |
| 2,575,163 | 11/1951 | Donovan | 604/394 |
| 2,854,979 | 10/1958 | Turner | 604/394 |
| 2,890,701 | 6/1959 | Weinman | 604/394 |
| 2,893,393 | 7/1959 | Pressley | 604/394 |
| 2,896,627 | 7/1959 | Harwood | 128/290 |
| 2,952,259 | 9/1960 | Burgeni | 128/290 |
| 3,224,448 | 12/1965 | Diebold | 128/529 |
| 3,400,718 | 9/1968 | Saijo | 604/394 |
| 3,800,797 | 4/1974 | Tunc | 128/290 R |
| 3,886,941 | 6/1975 | Duane et al. | 128/287 |
| 4,044,769 | 8/1977 | Papajohn | 128/288 |
| 4,215,692 | 8/1980 | Levesque | 604/904 |
| 4,301,550 | 11/1981 | Carver | 2/408 |
| 4,352,356 | 10/1982 | Tong | 128/288 |
| 4,421,512 | 12/1983 | Papajohn | 604/396 |
| 4,496,359 | 1/1985 | Pigneul | 604/387 |
| 4,579,556 | 4/1986 | McFarland | 604/385.2 |
| 4,617,022 | 10/1986 | Pigneul et al. | 604/394 |
| 4,619,862 | 10/1986 | Sokolowski et al. | 119/172 |
| 4,676,196 | 6/1987 | Lojek et al. | 119/171 |
| 4,695,279 | 8/1987 | Steer | 604/397 |
| 4,964,857 | 10/1990 | Osborn | 604/395 |
| 5,019,068 | 5/1991 | Perez et al. | 604/386 |
| 5,069,672 | 12/1991 | Wippler et al. | 604/387 |
| 5,167,653 | 12/1992 | Igaue et al. | 604/385.2 |

FOREIGN PATENT DOCUMENTS

| | | |
|---|---|---|
| 292464 | 8/1929 | United Kingdom . |
| 358765 | 10/1931 | United Kingdom . |
| 436869 | 10/1935 | United Kingdom . |
| 855020 | 11/1960 | United Kingdom . |
| 878455 | 9/1961 | United Kingdom . |
| 888827 | 2/1962 | United Kingdom . |
| 1143419 | 2/1969 | United Kingdom . |
| 1178212 | 1/1970 | United Kingdom . |
| 85/03430 | 8/1985 | WIPO . |

*Primary Examiner*—Randy C. Shay
*Attorney, Agent, or Firm*—Kenyon & Kenyon

[57] ABSTRACT

The present invention provides a washable diaper having a waterproof interior channel the walls of which are formed from the leg cuffs, for holding a removable absorbent insert, whether disposable or re-usable.

23 Claims, 6 Drawing Sheets

WASHABLE DIAPER WITH LIQUID IMPERVIOUS CHANNEL FOR RETAINING DISPOSABLE ABSORBENT INSERT

CROSS-REFERENCE TO RELATED APPLICATIONS

This application is a continuation-in-part of copending application Ser. No. 07/944,279 filed Sep. 14, 1992 entitled COMBINATION WASHABLE DIAPER WITH DISPOSABLE ABSORBENT INSERT which is in turn a continuation-in-part of co-pending application Ser. No. 07/921,579 filed Jul. 30, 1992 entitled ABSORBENT INSERT FOR DIAPERS AND INCONTINENT GARMENTS.

TECHNICAL FIELD

The invention relates to the construction of infant diapers.

BACKGROUND ART

A problem with existing infant diapers is that when disposable diapers are used, and the diaper is wetted or soiled even slightly, the entire diaper is discarded, at considerable expense and causing considerable waste. Fitted cloth diapers are less popular than disposable diapers due to their expense and the time and labour required to wash them, while non-fitted cloth diapers are difficult to fit to the infant, and also involve considerable labour to wash them. There is therefore a need for an infant diaper which combines the convenience of disposable diapers with the economy and environmental benefits of cloth diapers.

DISCLOSURE OF INVENTION

The present invention therefore provides a washable diaper having a waterproof interior pocket for holding a removable absorbent insert, whether disposable or re-usable. The insert may be bio-degradable and/or flushable. In the preferred form of the invention the waterproof interior channel is formed as a unitary welded channel having flanges running lengthwise along either side thereof which can in turn be stitched to the outer fabric shell of the diaper (or the crotch area of some other type of garment) without reducing the liquid imperviousness of the channel.

BRIEF DESCRIPTION OF DRAWINGS

In drawings which disclose a preferred embodiment of the invention.

BEST MODE(S) FOR CARRYING OUT THE INVENTION

Figure 1:
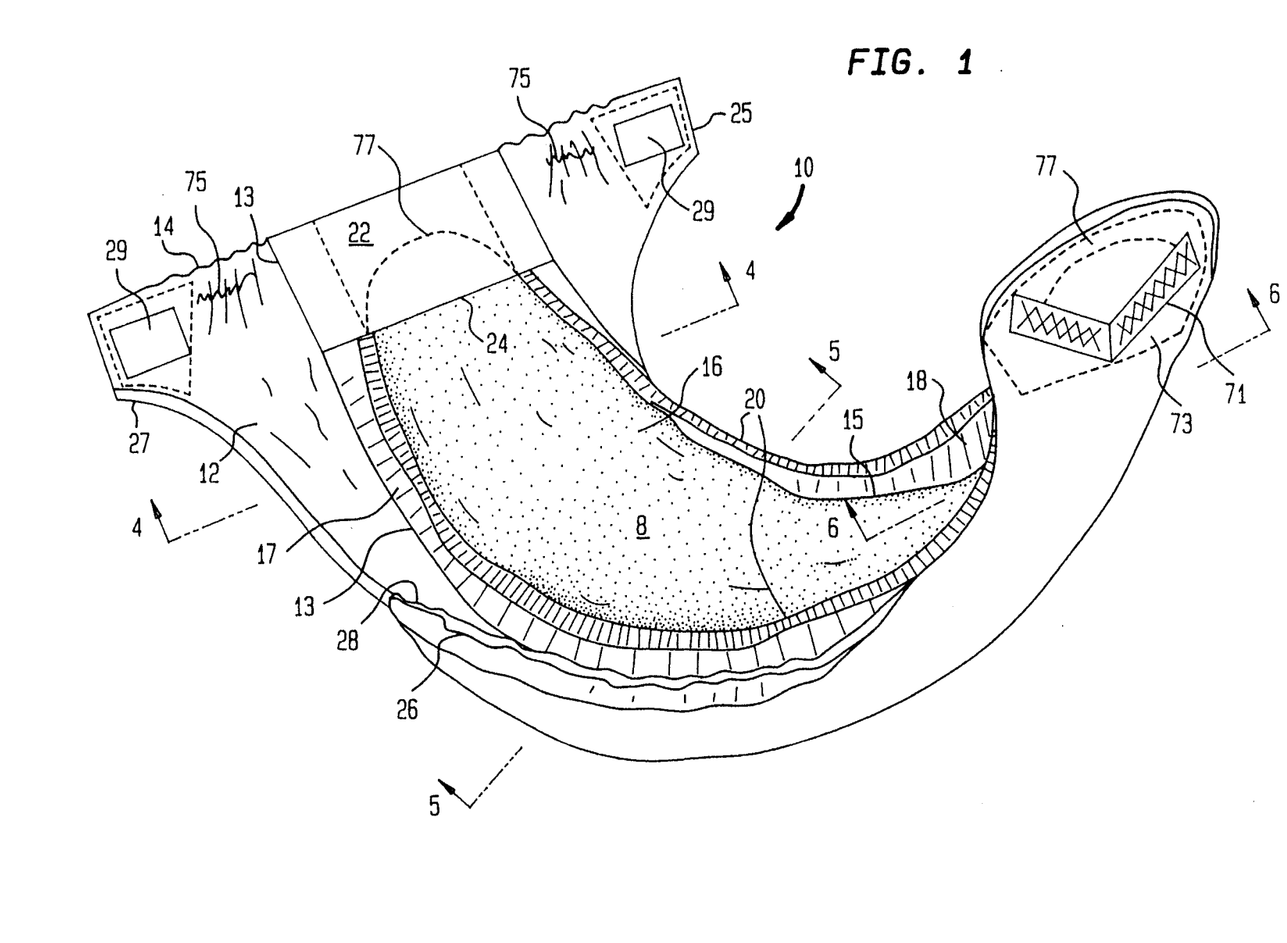
FIG. 1 is a perspective view of the infant diaper of the invention.
Figure 4:
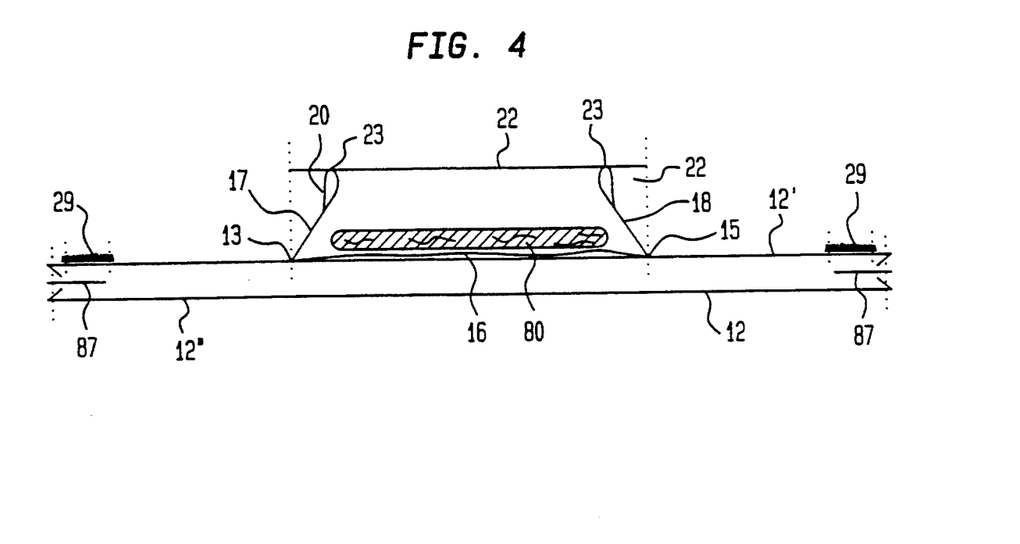
FIG. 4 is a cross-section taken along line 4—4 of FIG. 1.
Figure 5:
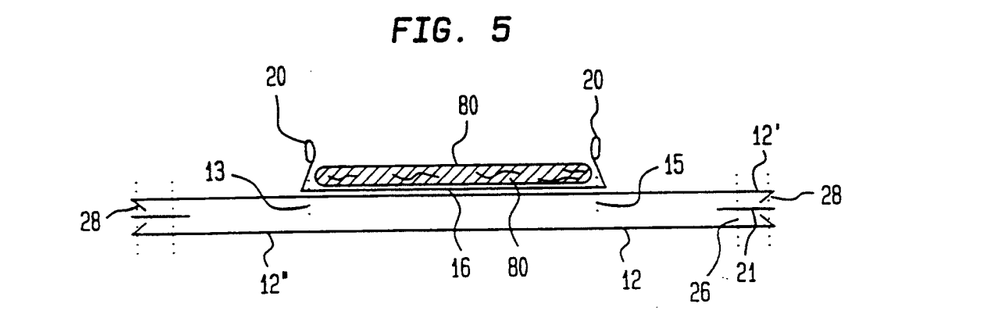
FIG. 5 is a cross-section taken along line 5—5 of FIG. 1.
Figure 6:
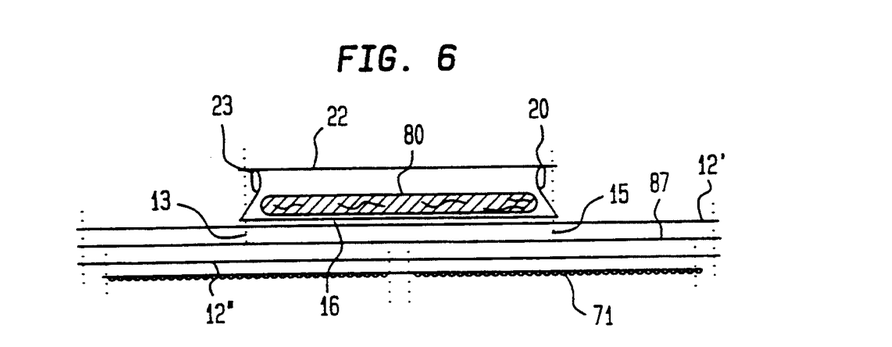
FIG. 6 is a cross-section taken along line 6—6 of FIG. 1.

FIG. 1 illustrates a novel reusable diaper 10 to be used, in place of existing disposable or fitted diapers, with a disposable or washable absorbent insert 80 (FIG. 4). It is constructed of an hour-glass shaped body 12 of a two-ply tight woven, breathable, water repellant 100% polyester micro-fibre fabric. The two panels 12', 12" (FIG. 4) are reverse stitched in that the outer edges are stitched together, and then the entire body is turned inside out. (In most instances where the term "stitched" is used herein it will be understood that equivalent processes such as serging, binding, gluing or sonic welding may also be used.) A top stitch is provided around the edges of rear end 14. A third waterproof interior ply 16 is provided forming a center waterproof channel or pocket 8. This third ply is a nylon fabric with a waterproof coating such as a polyurethane or polyvinyl chloride material and is connected to the top ply 12' of body 12 by stitching along lines 13, 15, forming raised waterproof side walls 17, 18 of the same polyurethane or polyvinyl chloride-coated nylon material. Walls 17, 18 are hemmed along their upstanding edges 20 with live rubber strips under tension and extending from edge 24 of panel 22 on the rear of the diaper to the lower edge of similar panel 22 on the front of the diaper. Edges 20 are stitched to the edges 24 of panels 22 at points 23 spaced inwardly from lines 13, 15.

The sides of body 12 are elasticized with elastic strips 21 stitched under tension between the outer and inner plies of material of the body 12 and stitched along lines 26 spaced inwardly from either leg-contacting edges 28 to create a soft edge. To provide the desired cupping of the diaper, the elastic strip along line 26 should also be spaced from the walls 17, 18.

Closure tabs 25 and 27 are provided with patches 29 of the hook portion of hook-and-loop fasteners which engage strips of the loop portion 71 on the front face 73 of the diaper. Alternatively, the hook-and-loop fasteners could be replaced with a double hook-and-eye metal fastener (two hooks and two eyes would be used, side by side, to prevent rotation of the fastener about the point of fastening). A metal hook-and-eye fastener has advantages over hook-and-loop fasteners in terms of durability under exposure to extreme heat and chemicals such as chlorine.

Elastic strips are stitched under tension between the two plies of body 12 at 75 to permit the tabs to stretch and apply pressure when attached. A third layer 87 of stiffening fabric may also be stitched between the two plies of body 12 in the area of tabs 25, 27 and front face 73 to provide a stiffening and smoother appearance.

For easier cleaning of the garment, as will be described in further detail below, the panels 22 at either end of the diaper are preferably sewn through the waterproof layer 16 and the two-ply body 12 along semicircular lines 77 at both ends. A waterproof channel or pocket 8 is thus formed along the central axis of the garment with its lower surface formed by waterproof fabric 16 and bordered at either end by stitch lines 77 and panels 22, and along either side by walls 17, 18.

To use the diaper, an absorbent insert 80 is inserted into pocket 8. Such insert is sized to fit snugly in pocket 8 and may be a disposable insert, or it may be a reusable, washable insert. In respect of a disposable insert 80, such insert may be manufactured from a super-absorbent polymer, including air-laid thermal-bonded materials of the type available for adult incontinence pads manufactured by Merfin Hygienic Products Ltd. The insert may be not only disposable but also flushable and biodegradable. ("Flushable" means the insert disintegrates in water to a particulate size which can be handled by a municipal sewage system.) For example a product marketed under the trademark PRIMA by Johnson & Johnson Inc. provides a bio-degradable absorbent pad for sanitary napkins and the like composed partly of peat moss. In such an application, an unused absorbent insert is inserted in pocket 8 with its ends under panels 22. The diaper is then placed on the infant in the usual way. Once the insert has been wetted or soiled, the insert is removed from the pocket 8 and either flushed down the toilet or placed in a waste disposal container. If the diaper 10 has been wetted or soiled it can be rinsed, and periodically will require washing. Stitching 77 may be used to prevent waste from getting in to square interior corners which would make cleaning more difficult.

Figure 2:
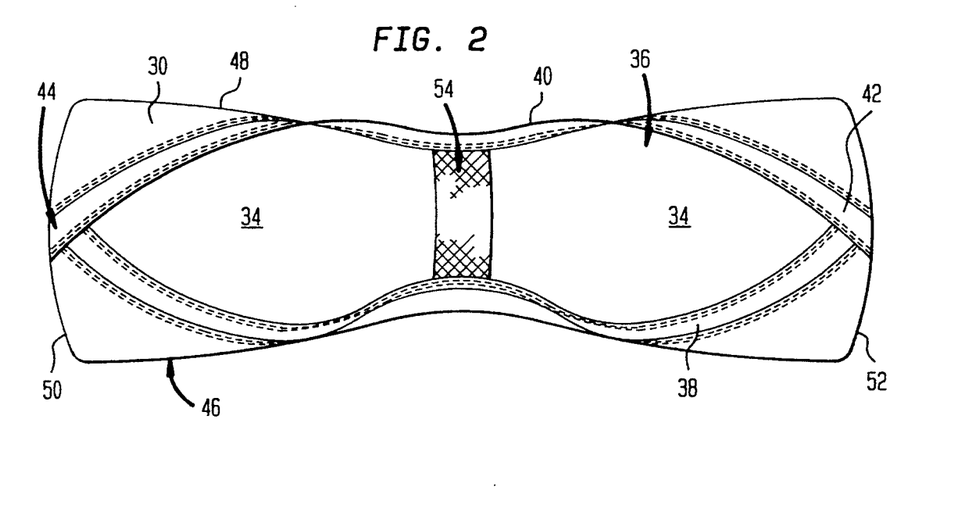
FIG. 2 is a plan view of an absorbent insert cover of the invention.

Re-usable inserts may also be used in the invention, and FIG. 2 illustrates an absorbent insert cover 30 which may be used to hold the absorbent insert 80 (whether disposable or washable) for insertion into pocket 8. The cover 30 is formed of a single piece of waterproof coated nylon 34, so that it is water impervious. A polyurethane or PVC coated nylon, washable and resistant to heat, bleach, detergent and ultra-violet radiation is suitable. It has a front opening 36 to receive and expose the absorbent insert, for example of the type illustrated as 32. The cover 30 has live (natural) rubber strips approximately 1 cm. in width hemming the edges 38, 40 of opening 36 which cross over at ends 42, 44 to provide a flatter profile. The cover is a one-piece construction so that edges 46, 48 are seamless to prevent leaking. Ends 50, 52 are waterproof seams formed by sonic welding or other waterproof seam means. An optional strip 54 of fast wicking spun polyester mesh is stitched at either end thereof to the inner edge (bottom) of rubber hem 38, 40 where they met the nylon backing material 34. Strip 54 does not stretch along its length, but may across its width in the longitudinal direction of the cover 30. As with the inserts, dimensions of the cover will vary according to the particular size of diaper.

Figure 3:
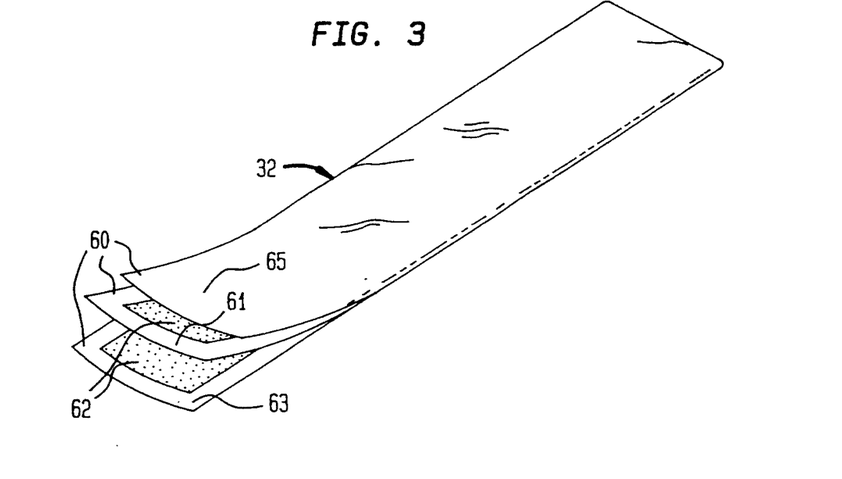
FIG. 3 is a perspective view of the absorbent insert of the invention.

FIG. 3 illustrates one embodiment of the absorbent reusable insert 32 which may be used alone or in the cover 30. Insert 32 is formed of three layers 60 of brushed polyester, and two layers 62 of absorbent felt. The two felt layers 62 are slightly narrower than the polyester layers 60, and are secured to the central polyester layer 61 by stitching along either longitudinal edge which extends through only felt layers 62 and layer 61. The three-piece sandwich thus formed is then in turn contained between layers 63, 65 by stitching which extends only through the outer edges of layers 61, 63, 65. This creates a softer outer edge of the insert. Sharp edges are further avoided by staggering the ends of layers 62.

Another form of insert 32 which can be used in the invention is a single layer of absorbent felt material covered with a non-wicking "stay dry" material such as polyester. The felt layer may be 100% rayon, a blend of rayon and polyester, or a microporous acrylic such as that sold under the trademark SUPERSORB. As an alternative to the felt layer, a multiple layer of cotton fabric, of a flannelette or bird's eye weave, may be used.

When used in cover 30, insert 32 is inserted to fit smoothly in the interior of cover 30, and cover 30 is inserted into pocket 8 of the diaper 10 with opening 36 pointing towards the interior of the garment. Due to the curvature of the garment, the dimensions of edges 38, 40 and the tightening action of strip 54, the edges 38, 40 are caused to be raised in relation to insert 30. This causes a damming effect on liquid within cover 30. The waterproof container formed by cover 30 allows time for the liquid to be absorbed by the absorbent insert. Squeezing of cover 30 may cause liquid to exit from insert 32 but it will still be retained in cover 30 and reabsorbed into the insert when pressure is released. After the insert has been wetted, the garment is removed, the cover slipped out of the garment, the cover is rinsed or washed in warm water, the insert is replaced with a clean insert (or the insert in question is washed), and the cover is replaced in the garment. The waterproof cover allows the saturated inserts to be removed with minimum contact of the user's hands.

The cover 30 permits any number of inserts to be inserted into the cover depending on the user's needs. In each case, the cover is readily inserted like a cassette, regardless of the number of absorbent inserts. The low friction coating of the cover makes this insertion easier. Thus by using the cover 30 of the invention and either a reusable or disposable insert, soiling of diaper 10 is further reduced and the diaper can be re-used a number of times without washing. The user simply inserts the cover with the desired type and number of inserts in the crotch area of the diaper, opening inwardly, and puts the diaper on the infant in the usual way. The cover 30 (and insert) need not be hour-glass shaped as shown, but rather can have straight, parallel sides.

FIG. 7 through 13 illustrate a preferred manner of forming the waterproof channel and attaching it to the fabric body 12 of the diaper. In the embodiment shown in FIG. 7 and 8, the body 12 is preferably formed again of a layer 100 of a tight woven, breathable, water repellant 100% polyester fabric, woven from a micro-fibre or a high multi-filament count polyester yarn. This provides a soft comfortable finish to the diaper. The center waterproof channel or pocket 108 is formed again of a nylon fabric 109 with a waterproof coating such as a polyurethane or polyvinyl chloride material and is formed with unitary walls 117, 118 by forming flanges 120, 122 and sonic welding along lines 123, 125 to weld the upper ply of the flange to the lower ply along the lower edge of the wall. The ends of the channel 108 are folded over to form panel 132 which may be stitched to the underlying material 109 along semicircular line 133 to prevent waste from getting in to square interior corners which would make cleaning more difficult. Walls 117, 118 are again hemmed along their upstanding edges 130 with live rubber strips under tension and are connected to panel 132 at stitches 136 and extend to the lower edge of a similar panel on the other end of the channel (not shown).

Figure 7:
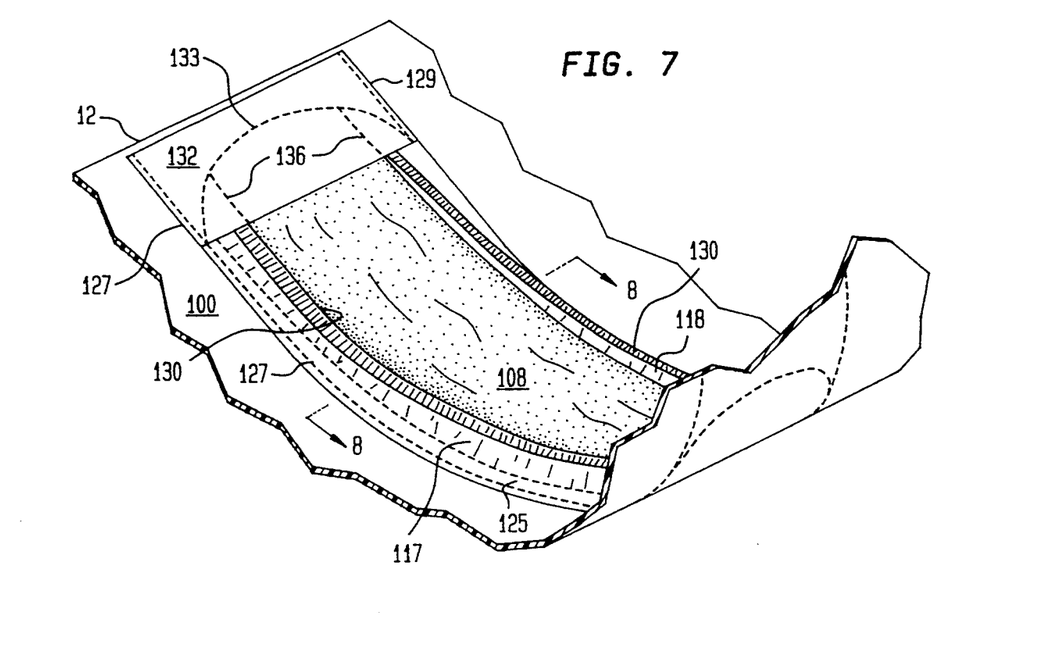
FIG. 7 is a partial perspective view of a preferred construction of the waterproof channel of the invention attached to the body of the diaper.
Figure 8:
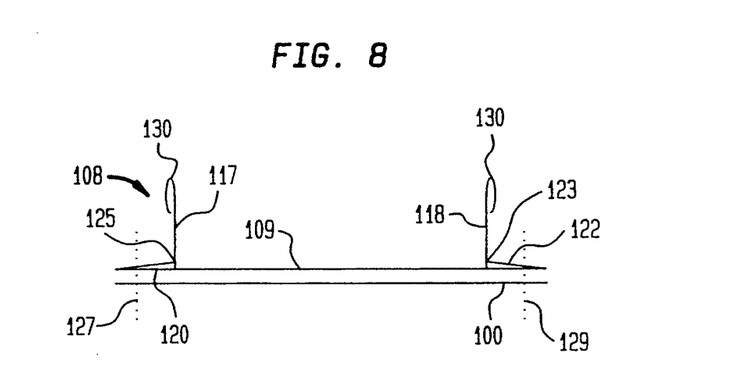
FIG. 8 is a cross-section taken along line 8—8 of FIG. 7, showing a first embodiment of the means of attachment.

The material 109 can then be connected to the body 100 by stitching through flanges 120, 122 along lines 127, 129 without the stitches extending through the central channel 108. In this way the water impervious central channel 108 can be secured to a non-waterproof outer shell by stitching without affecting the water imperviousness of the central channel.

Figure 9:
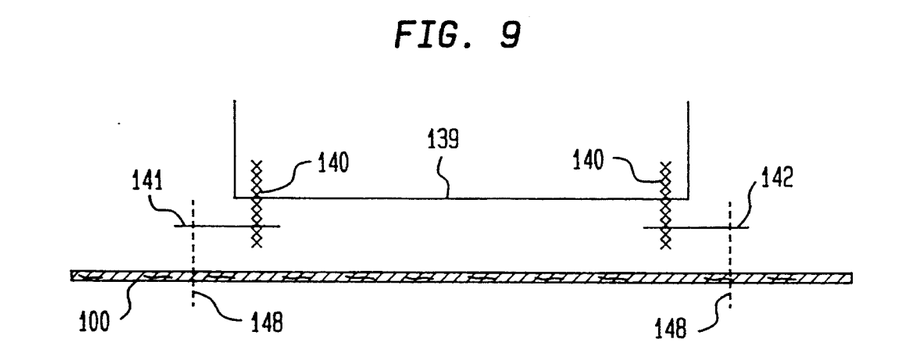
FIG. 9 is a cross-section taken along line 8—8 of FIG. 7 showing a second embodiment of the means of attachment.
Figure 10:
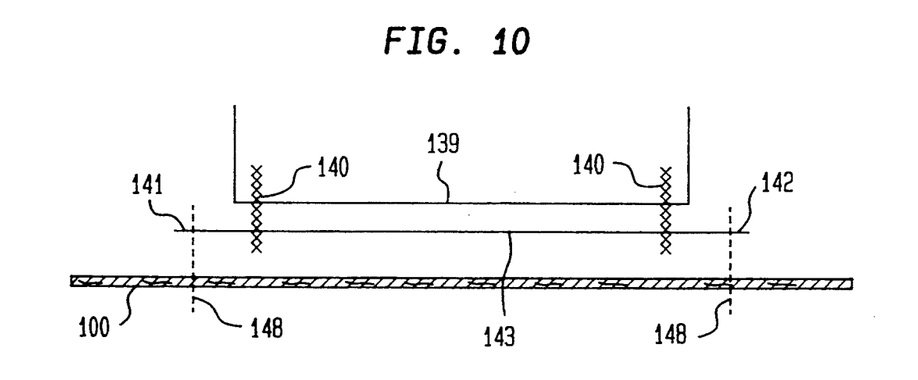
FIG. 10 is a cross-section taken along line 8—8 of FIG. 7 showing a third embodiment of the means of attachment.
Figure 11:
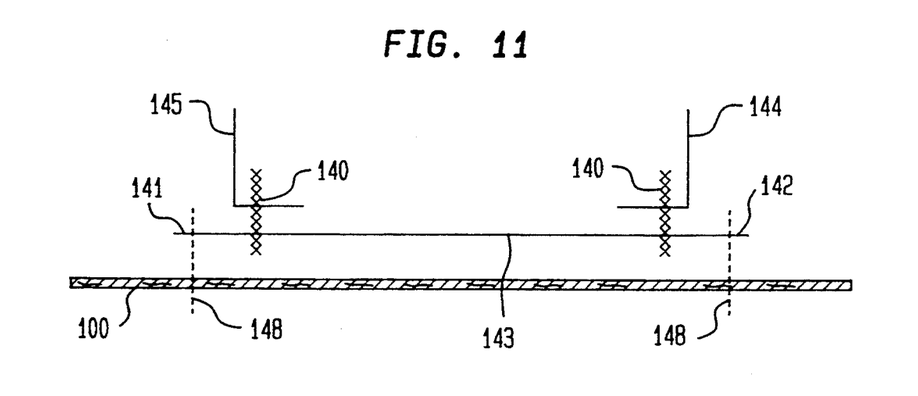
FIG. 11 is a cross-section taken along line 8—8 of FIG. 7 showing a fourth embodiment of the means of attachment.
Figure 12:
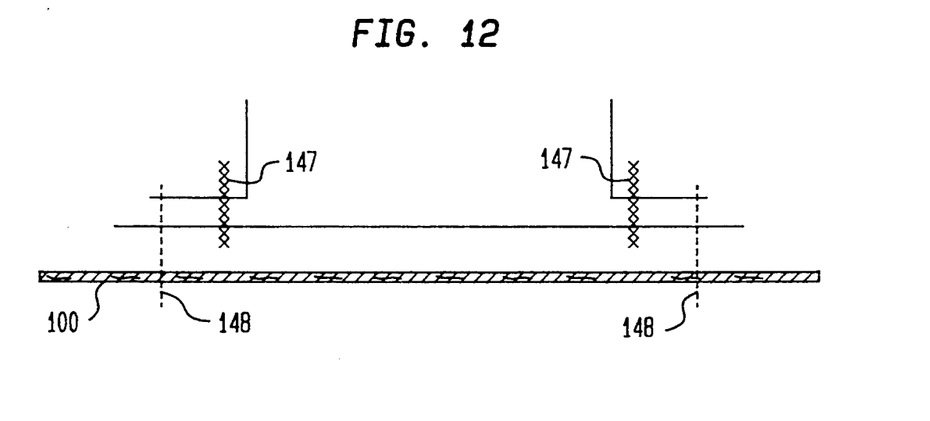
FIG. 12 is a cross-section taken along line 8—8 of FIG. 7 showing a fifth embodiment of the means of attachment.
Figure 13:
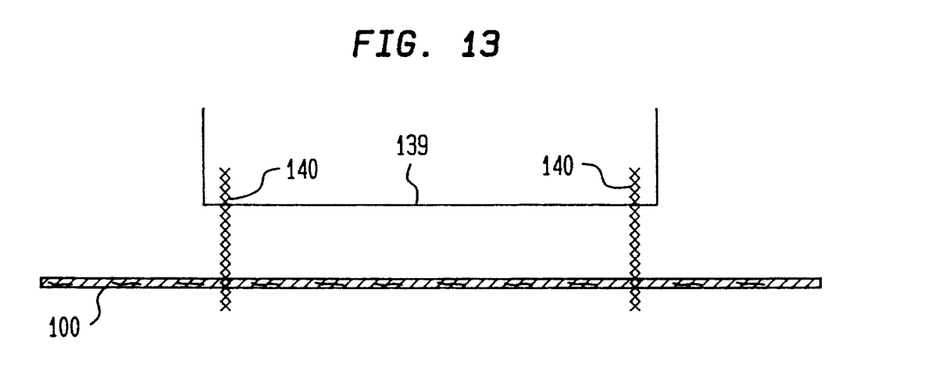
FIG. 13 is a cross-section taken along line 8—8 of FIG. 7 showing a sixth embodiment of the means of attachment.

FIGS. 9 through 13 illustrate other methods of achieving the same functional result as in FIG. 8. In FIG. 9, a central rectangular channel 139 of liquid impermeable material is welded or glued at seams 140 to two parallel strips 141, 142 of the same material. The outer edges of strips 141, 142 are then stitched to the underlying fabric body 100 along lines 148. In FIG. 10, strips 141, 142 are replaced with a sheet 143 which extends beyond the edges of the central channel 139. In FIG. 11, the central channel 139 is formed by welding or gluing two L-shaped walls 144, 145 to sheet 143, with the outer edges of sheet 143 being stitched to the underlying fabric. In FIG. 12, the lower horizontal portions of walls 144, 145 extends outwardly to form part of the outer flanges, so the welding will run akong lines 147 and stitching to the underlying body along 148. Of course if the outer body material 100 is suitable, the channel 139 may be welded directly to it as in FIG. 13, but generally it will be preferable to haver a soft fabric for outer shell 100 which is not compatible with welding.

Since the waterproof channel in the embodiments shown in FIG. 7-13 forms an independent element separate from the diaper, it could similarly be attached to the crotch area of other types of garments to permit insertion of an absorbent pad, such as underwear, bathing suits and the like.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. An incontinence garment comprising a pliant body for removable fitting to a wearer, said body having an interior and an exterior surface and a front and back portion and a crotch area, said garment comprising opposed elastically contractible leg cuffs extending between said front and back portions, said garment also comprising a non-absorbent, liquid impervious channel secured to said interior surface in the crotch area of said body extending between said front and back portions and opening to the interior of said body, said channel being adapted for removably receiving an absorbent insert and comprising a liquid impervious central section and two opposed generally upstanding liquid impervious walls along opposed edges of said central section, the garment further comprising an absorbent insert removably contained in the liquid impervious channel.

2. The garment of claim 1 wherein said pliant body is a fabric.

3. The garment of claim 1 wherein said upstanding walls project upwardly from said elastically contractible cuffs.

4. The garment of claim 1 wherein said walls include inner edges and are provided with elasticized hems along said inner edges.

5. The garment of claim 4 wherein a panel extends across either end of said channel between said hems forming a recess.

6. The garment of claim 5 wherein said panel is secured to said liquid impervious layer by a curved end stitch.

7. The garment of claim 1 wherein said channel comprises flanges extending along either edge thereof and said channel is secured to said interior surface of said body along said flanges.

8. The garment of claim 8 wherein said walls of said channel and said flanges are formed by sonic welding of said liquid impervious walls to said liquid impervious central section along the lower edges of said walls.

9. The garment of claim 1, further comprising a cover for said absorbent insert, said cover being adapted for placement in said channel, said cover comprising a liquid impervious material forming an elongated pocket, said pocket including a front face and having an opening across a major portion of the front face, said pocket having an edge at said opening and a raised rim extending around said edge.

10. The garment of claim 1, wherein said insert comprises two absorbent layers, a central web having an outer edge, and two outer layers having edges, and wherein said two absorbent layers are secured to either face of said central web, and said two outer layers secured to each other and the outer edge of said central web along the edges of said outer layers.

11. The garment according to claim 1 wherein the pliant body is not waterproof.

12. The garment according to claim 1 wherein said two opposed walls extend along opposite sides of said central section between said front and back portions of the garment.

13. The garment according to claim 1 wherein said central section is generally rectangular in shape and is disposed generally longitudinally in the garment, extending between the front and back portions of the garment.

14. An incontinence garment comprising a washable fabric body for removable fitting to a wearer, said body having an interior and an exterior surface and a front and back portion and a crotch area, said garment comprising a non-absorbent, liquid impervious channel secured to said interior surface in the crotch area of said body extending longitudinally between said front and back portions and opening to the interior of said body, said channel having a central section adapted for removably receiving an absorbent insert and two opposed generally upstanding, longitudinally extending walls along opposed edges of said central section, the garment further comprising an absorbent insert removably contained in the liquid impervious channel.

15. The garment of claim 14 wherein said insert is non-washable.

16. The garment of claim 14, wherein said insert is composed of a bio-degradable material.

17. The garment of claim 16, wherein said insert is composed of a bio-degradable material containing peat moss.

18. The garment according to claim 14 wherein the fabric body is not waterproof.

19. The garment according to claim 14 wherein said walls are provided with elasticized hems along upper edges of the walls.

20. A non-absorbent, liquid impervious channel adapted for being secured to an interior crotch area of a garment, said channel having a central section adapted for removably receiving an absorbent insert and two opposed, generally upstanding walls comprising opposed elastically contractible leg cuffs extending along opposed edges of said central section wherein said channel further comprises flanges extending along either edge thereof adapted for being secured to said garment.

21. The channel of claim 20 wherein said walls are provided with hems and wherein the channel includes opposite ends and further comprising two panels extending across the ends of said channel between said hems forming recesses at either end thereof.

22. The liquid impervious channel according to claim 20 wherein the channel is adapted for being secured to the crotch area of a garment that is not waterproof.

23. The liquid impervious channel of claim 20 wherein said walls are provided with elasticized hems along upper edges of the walls.

* * * * *

UNITED STATES PATENT AND TRADEMARK OFFICE
CERTIFICATE OF CORRECTION

PATENT No. : 5,360,422

DATED : November 1, 1994

INVENTOR(S): James R. Brownlee and William E. Lasby

It is certified that error appears in the above-identified patent and that said Letters Patent is hereby corrected as shown below:

Column 5, line 29, "akong" should be --along--;

Column 5, line 33, "haver" should be --have--; and

Column 6, line 17, "The garment of claim 8" should be --The garment of claim 7--.

Signed and Sealed this

Thirtieth Day of April, 1996

Attest:

BRUCE LEHMAN

*Attesting Officer*   *Commissioner of Patents and Trademarks*